United States Patent [19]

Matsuda et al.

[11] Patent Number: 5,718,723
[45] Date of Patent: Feb. 17, 1998

[54] ARTIFICIAL BLOOD VESSEL AND PROCESS FOR PRODUCING THE SAME

[75] Inventors: Takehisa Matsuda, Osaka; Nobuyuki Nakajima, Chiba; Hiroyuki Kito, Tokyo, all of Japan

[73] Assignee: Seikagaku Kogyo Kabushiki Kaisha (Seikagaku Corporation), Tokyo, Japan

[21] Appl. No.: 305,377

[22] Filed: Sep. 13, 1994

[30] Foreign Application Priority Data

Mar. 15, 1994 [JP] Japan .................... 6-068927

[51] Int. Cl.$^6$ .................... A61F 2/06; A61F 2/04
[52] U.S. Cl. .................... 623/1; 623/12; 600/36
[58] Field of Search .................... 623/1, 11, 12, 623/66; 606/191–200, 152–154, 158; 604/96, 8; 600/36

[56] References Cited

U.S. PATENT DOCUMENTS

| | | | |
|---|---|---|---|
| 3,960,685 | 6/1976 | Sano et al. | 204/159.12 |
| 4,321,711 | 3/1982 | Mano | 3/1.4 |
| 4,784,659 | 11/1988 | Fleckenstein et al. | 623/1 |
| 4,863,907 | 9/1989 | Sakurai et al. | 514/56 |
| 4,902,290 | 2/1990 | Fleckenstein et al. | 623/1 |
| 4,973,493 | 11/1990 | Guire | 427/2 |
| 4,979,959 | 12/1990 | Guire | 623/66 |
| 5,028,597 | 7/1991 | Kodama et al. | 514/56 |
| 5,116,824 | 5/1992 | Miyata et al. | 514/55 |

FOREIGN PATENT DOCUMENTS

| | | |
|---|---|---|
| 3531547 | 3/1993 | European Pat. Off. |
| A10531547 | 3/1993 | European Pat. Off. |
| A20554898 | 8/1993 | European Pat. Off. |
| A13912122 | 10/1990 | Germany |
| 6226230 | 4/1987 | Japan |
| 6255426 | 11/1987 | Japan |
| 6344383 | 9/1988 | Japan |
| 2270823 | 2/1990 | Japan |
| 3280949 | 11/1991 | Japan |
| 372300 | 11/1991 | Japan |
| 4300537 | 10/1992 | Japan |
| 4300559 | 10/1992 | Japan |
| 576588 | 3/1993 | Japan |
| 5269196 | 10/1993 | Japan |

OTHER PUBLICATIONS

Shimomura et al., "Photochemical Reaction of Stilbazole Amphiphile in Cast Orientated Film," The Chemical Society of Japan, 10:1185–1188 (1990).

The Japanese Society of Gastroenterological Surgery, The Japanese Journal of Gastroenterological Surgery, vol. 25, No. 6, 1992, p. 1509.

Primary Examiner—Debra S. Brittingham
Attorney, Agent, or Firm—Sughrue, Mion, Zinn, Macpeak & Seas

[57] ABSTRACT

This invention provides a more functionalized artificial blood vessel which can be organized by independently designing its inner and outer surfaces and endowing them with respectively different biocompatibilities, as well as a process for producing the same.

The artificial blood vessel comprises a tubular support having a layer of photogelled cinnamic acid-bound chondroitin sulfate coated on the inner surface thereof and a layer of photogelled coumarin-bound gelatin coated on the outer surface thereof. The process for producing the above artificial blood vessel comprises coating a layer of coumarin-bound gelatin on the outer surface of a tubular support and a layer of cinnamic acid-bound chondroitin sulfate on the inner surface of the support and irradiating each of the layers with light.

8 Claims, 2 Drawing Sheets

ARTIFICIAL BLOOD VESSEL AND PROCESS FOR PRODUCING THE SAME

FIELD OF THE INVENTION

This invention relates to the improvement of artificial blood vessels.

BACKGROUND OF THE INVENTION

Various types of artificial blood vessels are used as substitute blood vessels for the treatment of vascular diseases. Since artificial blood vessels are implanted in the living body, extremely strict properties are required for their materials, such as the absence of toxicity, antigenicity, thrombogenesis and the like and sufficient durability.

Artificial blood vessels are usually composed of woven or knitted fabric and have high porosity. They are used generally after formation of fibrin coat membrane by carrying out pre-clotting treatment using autoblood in order to prevent leakage of blood. However, operation of the pre-clotting treatment is complex and there is a possible danger that the fibrin coat membrane peels off due to the acceleration of postoperative fibrinolysis. In addition, especially in the case of a small bore artificial blood vessel having an inside diameter of about 6 mm or less, it has a disadvantage that the inside of the artificial blood vessel is obstructed by the fibrin coat membrane formed on its inner surface.

In order to gain high grade functions of artificial blood vessels, sealing grafts obtained by coating porous artificial blood vessels with collagen, gelatin, albumin and the like, without the pre-clotting treatment, are used clinically [Reid D.B. and Pollock J.G.: A Prospective Study of 100 Gelatin-Sealed Aortic Grafts; Ann. Vasc. Surg., 5, 320 (1991)]. It is emphasized that these artificial blood vessels have a healing-accelerating function in addition to their sealing function. In addition, it has been reported that anti-thrombogenic property of artificial blood vessels can be improved at least at experimental level by fixing or impregnating heparin by various means.

Also, JP-B-62-55426 (the term "JP-B" as used herein means an "examined published Japanese patent application") discloses that an artificial blood vessel having anti-thrombogenic property and excellent adhesiveness to biological tissues can be produced by coating the inner surface of a specified flexible polymer tube with an anti-thrombogenic material, and the outer surface with collagen or gelatin.

However, though this artificial blood vessel has excellent adhesiveness to endothelial cells, the high platelet tackiness entails a problem of causing obstruction of the artificial blood vessel by thrombus prior to the proliferation of endothelial cells on the inner surface. In addition, it also has other problems to be solved with regard to foreign body reaction, fervescence, peeling of coated material, antigenicity, toxicity, durability, inflammatory reaction, safety and the like.

A therapeutically desired artificial blood vessel is to be organized by covering it with stable connective tissues from both inner and outer sides of the vessel (Sauvage L.R.: Biologic Behavior of Graft in Arterial System; Vascular Surgery, ed. by Haimovici H., Appleton & Lange, Connecticut, 136, 1989). That is, it is ideal for an artificial blood vessel to gain an autonomic state by covering its inner surface with spurious intimal membrane tissues lined by a layer of endothelial cells and its outer surface with connective tissues penetrated into fiber gaps. For this purpose, it is required that anti-thrombogenic property and penetration of endothelial cells should not be prevented until the inner surface of the artificial blood vessel is covered with endothelial cells. It is also required that tissues quickly penetrates into interfibrous gaps of the vessel from its outer surface. In other words, at the cellular level, non-adhesiveness is required for the inner surface of the artificial blood vessel in order to prevent adhesion of platelets, leukocytes and the like, and adhesiveness, migration and proliferation of fibroblasts and the like are required for the outer surface of the vessel.

Hence directly opposite cellular responses are required for the inner and outer sides of each artificial blood vessel and, in order to satisfy such requirements, it is necessary to optimize designs of the inner and outer sides of the artificial blood vessel. In consequence, recently the development of techniques which render such designing possible is highly desired.

SUMMARY OF THE INVENTION

An object of the present invention is to provide a more functionalized artificial blood vessel which can be organized by independently designing its inner (luminal) and outer surfaces and endowing them with respectively different biocompatibilities, as well as a process for producing the same.

The above object of the present invention has been achieved by gelation of two kinds of extracellular matrices (to be referred to as "ECM" hereinafter), chondroitin sulfate and gelatin, having different cell reactivities through a photoreaction and thus respectively insolubilizing them on the inner and outer surfaces of an artificial blood vessel in order to embody the design concept endowing inner and outer surfaces with different biocompatibilities.

More specifically, the present invention provides an artificial blood vessel which comprises a tubular support having a layer of photogelled cinnamic acid-bound chondroitin sulfate coated on the inner surface thereof and a layer of photogelled coumarin-bound gelatin coated on the outer surface thereof. The present invention also provides a process for producing the above artificial blood vessel which comprises coating a layer of coumarin-bound gelatin on the outer surface of a tubular support and a layer of cinnamic acid-bound chondroitin sulfate on the inner surface of the support, and irradiating each of the layers with light.

Other objects and advantages of the present invention will be made apparent as the description progresses.

Figure 1:
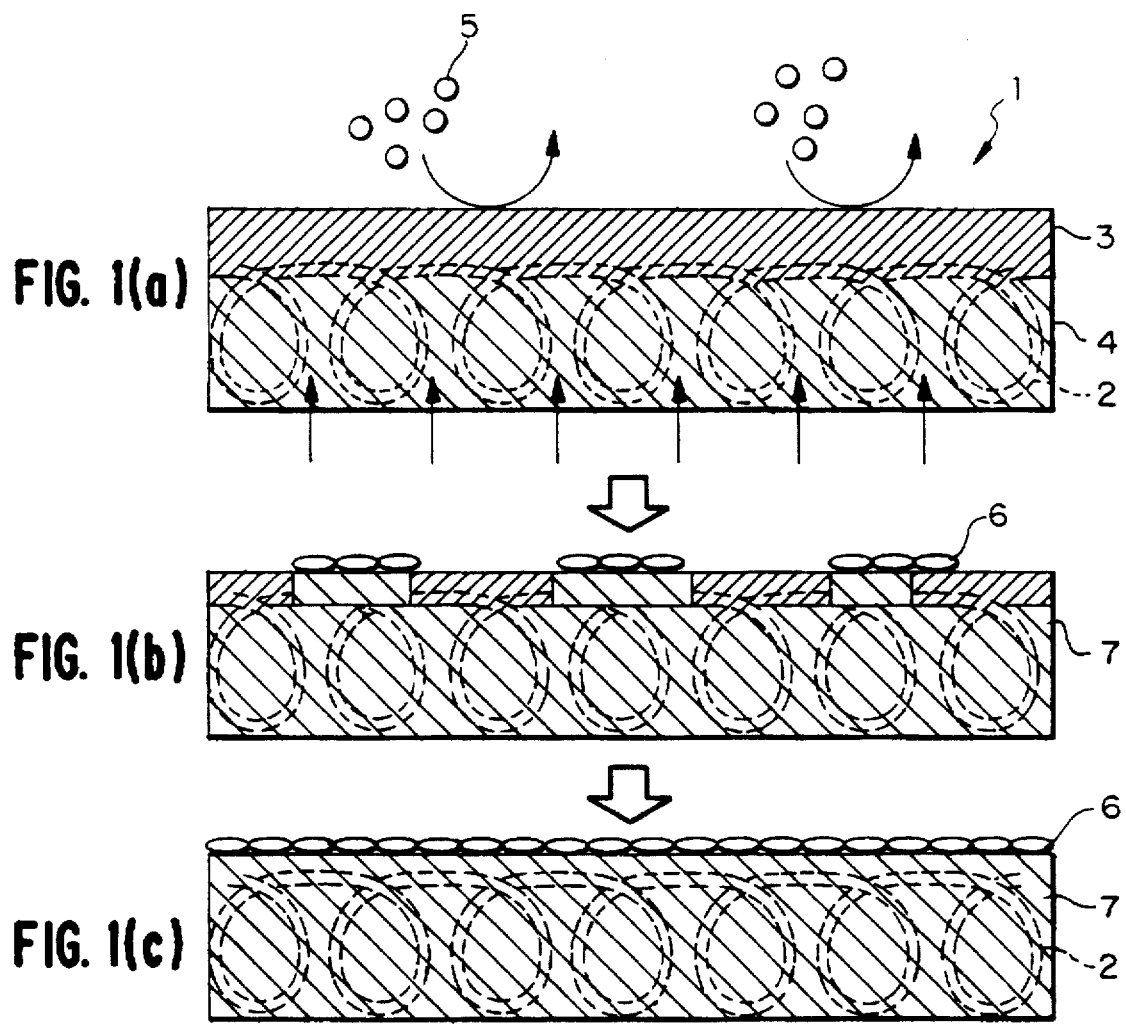
FIG. 1 schematically shows function of the artificial blood vessel of the present invention.

In these drawings, 1 represents an artificial blood vessel, 2 represents a support, 3 represents a photogelled C-CS layer, 4 represents a photogelled C-GT layer, 5 represents platelets and the like, 6 represents endothelial cells, 7 represents connective tissues (cells), 10 represents chondroitin sulfate (CS) or gelatin (GT), 11 represents photodimerizable cinnamoyl group (A) represented by the formula or coumaryloxymethylcarbonyl group (B) represented by the formula,

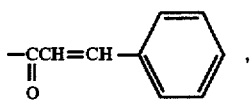

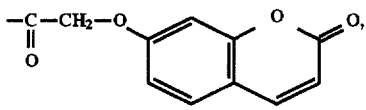

12 represents C-CS or C-GT molecule, 13 represents an photodimerized product (C) represented by the formula,

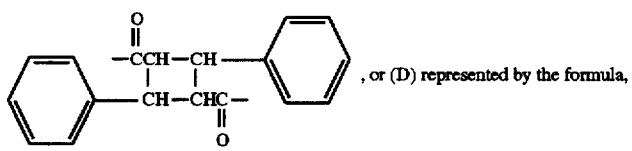, or (D) represented by the formula,

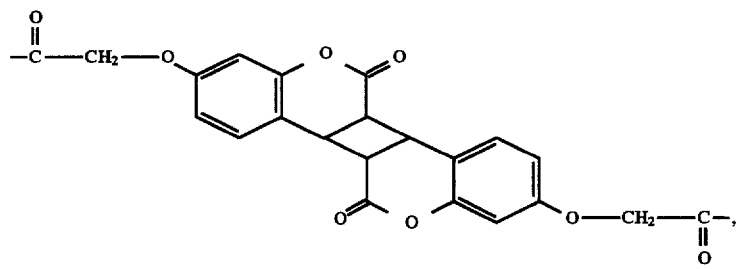

20 represents an ultraviolet light irradiation apparatus, 21 represents an optical probe made of quartz, 22 represents cooling water and 23 represents mercury-xenon lamp.

DETAILED DESCRIPTION OF THE INVENTION

The artificial blood vessel of the present invention has been developed taking notice of different organization steps inside and outside the vessel and on the basis of the findings that, when specified biopolymers having different functions are used, inside the vessel adhesion of blood components such as platelets leukocytes and the like to the inner surface of the vessel can be inhibited effectively, patency of the vessel can therefore be improved and biodegradation inside the vessel can be effected at an appropriate rate, whereas outside the vessel adhesiveness of cells such as fibroblasts, capillary endothelial cells and the like to the biopolymer, biodegradation of the biopolymer at an appropriate rate and migratory function of these cells can be improved effectively on the outer surface of the vessel, as well as improved biocompatibility and substitution of the biopolymer by the above-mentioned cells, hence rendering possible organization of the vessel.

Basic design concept of the artificial blood vessel of the present invention is to make up the inner surface of the artificial blood vessel by a cell non-adhesive ECM layer insolubilized by gelation through photodimerization of photoreactive groups, and the outer surface of the vessel by a cell adhesive ECM layer insolubilized by the same photogelation. Various known photoreactive groups and ECMs can be used within the range of the above design concept of the present invention.

More illustratively, the inner layer of the artificial blood vessel of the present invention is composed basically of photogelled cinnamic acid-modified chondroitin sulfate (photogelled C-CS), and the outer layer of the vessel is composed of photogelled coumarin-modified gelatin (photogelled C-GT). In this instance, each layer may be optionally contained with other chemical substances, biological cells and the like than the photogelled ECM, provided that they do not spoil the object of the present invention.

Chondroitin sulfate (CS) as the main skeleton of the cinnamic acid-modified chondroitin sulfate (C-CS) can endow the inner layer of the artificial blood vessel with cellular non-adhesiveness because of its high hydrophilic nature and can show heparin-like anticoagulant activity, while gelatin (GT) as the main skeleton of the outer layer coumarin-modified gelatin (C-GT) is a cell adhesive protein. Both of these compounds are major extracellular matrices (ECM) which constitute blood vessel walls.

C-CS is a compound obtained by introducing a photo-crosslinking group (photoreactive group), namely a photo-dimerizable cinnamoyl group (Cin group), into CS, and C-GT is a compound obtained by introducing a photodimer-izable coumaryloxymethylcarbonyl group (Cou group) into GT. That is, in the artificial blood vessel of the present invention, each layer composed of C-CS or C-GT is irradiated with light to effect dimerization of the Cin groups or Cou groups, and the water insoluble gel layers thus formed are intended to use as artificial extracellular matrices.

The following describes function of the artificial blood vessel of the present invention by reference to FIG. 1.

FIG. 1 schematically illustrates periodical changes in sections of the artificial blood vessel of the present invention after its implantation into the living body.

As shown in (a), the artificial blood vessel 1 of the present invention at an early stage of the implantation is composed of a support 2, a photogelled C-CS layer 3 and a photogelled C-GT layer 4, and the surface of the photogelled C-CS layer 3 contacts with blood to maintain anti-thrombogenic property by preventing adhesion of platelets and the like 5, while the photogelled C-GT layer 4 contacts with biological tissues and adheres fibroblasts and the like, at the same time effecting migration of cells from the tissue side toward the arrowhead direction thereby allowing tissues to proliferate inward. After a lapse of time as shown in (b), the photogelled C-CS layer 3 is biologically decomposed while maintaining its anti-thrombogenic property, the inner surface of the artificial blood vessel is partly covered with endothelial cells 6 which are supplied from capillary vessels or anastomotic moieties (not shown in the drawing) penetrated from the outside after biodegradation of the photogelled C-GT layer 4 that is simultaneously substituted by connective tissues 7. After a further lapse of time as shown in (c), the photogelled C-CS layer 3 is substituted by connective tissues 7 and entire area of the inner surface is covered with endothelial cells 6, thus showing complete biodegradation of the photogelled C-CS layer 3 and the photogelled C-GT layer 4 of the present invention and complete reconstruction of original blood vessel tissues except for the support 2, namely organization of the artificial blood vessel.

The C-CS to be used in the present invention can be synthesized in accordance with known method such as a process disclosed in EP-A 2-0554898 or in *Jinko Zoki* (Artificial Organs), 22(2), 376–379 (1993). For example, C-CS can be synthesized by allowing tri-n-butylamine salt of CS to react with cinnamoyl chloride in N,N-dimethylformamide to form ester bonding between the hydroxyl group of CS and cinnamoyl group.

The CS to be used in the present invention is not particularly limited and examples thereof include those which have been extracted and purified from connective tissues such as cartilage, trachea, aorta, dermis, tendon, umbilical cord, notochord and the like of animals belonging to Mammalia, Pisces and Cephalopoda and commercially available products (manufactured for instance by Seikagaku Corporation). Preferred as the CS are those derived from cartilage, skin or notochord of shark, sturgeon, whale, bovine, squid or the like. The molecular weight of the CS can be selected depending on the object. In general, the molecular weight of the CS may be within the range from 2,000 to 100,000, preferably from 10,000 to 80,000. Specific examples thereof include chondroitin sulfate A, chondroitin sulfate B (dermatan sulfate), chondroitin sulfate D and chondroitin sulfate E.

The C-GT having Cou group can be obtained by allowing amino group of GT and carboxyl group of 7-coumaryloxyacetic acid to react with a water soluble carbodiimide (for example, 1-ethyl-3-(3-dimethylaminopropyl)carbodiimide hydrochloride) in an aqueous medium, thereby forming an amide bonding.

The GT to be used in the present invention is not particularly limited and its examples include those which have been extracted and purified from bones, sinews, dermis and the like of mammals such as bovine, swine and the like and commercially available products (manufactured for instance by Wako Pure Chemical Industries, Ltd. or Nitta Gelatine Co., Ltd.).

According to the present invention, the number of photodimerizable groups introduced into C-CS or C-GT can be selected depending on the object. In general, C-CS may contain introduced Cin groups within the range of from 0.01 to 3.0 groups, preferably from 0.5 to 3.0 groups, per constitutive disaccharide repeat unit, and C-GT may contain introduced Cou groups within the range of from 5 to 50 groups, preferably from 15 to 45 groups, per molecule.

According to the present invention, the photogelled C-CS is synthesized through dimerization reaction of Cin groups by irradiating C-CS with light, preferably ultraviolet light, more preferably ultraviolet light from which beams having wave lengths of not more than 270 nm are removed, for a required period of time, generally from 5 to 30 minutes. By selecting the irradiation time and the number of Cin groups to be introduced, crosslinking ratio and gelling ratio, or cellular adhesiveness and rigidity can be controlled. In the same manner, the photogelled C-GT is synthesized through dimerization reaction of Cou groups by irradiating C-GT with light, preferably ultraviolet light, more preferably ultraviolet light from which beams having wave lengths of not more than 310 nm are removed, for a required period of time, generally from 5 to 30 minutes. By selecting the irradiation time and the number of Cou groups to be introduced, crosslinking ratio, gelling ratio, cellular adhesiveness and rigidity can be controlled.

In other words, swelling ratio of each of these photogelled matrices which exerts influences upon rigidity can be controlled by properly selecting introducing ratio of the photocrosslinking groups (photoreactive groups) and ultraviolet light irradiation time.

Figure 3:
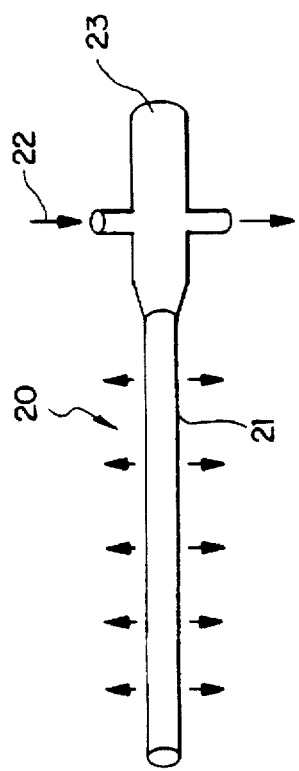
FIG. 3 shows an ultraviolet light irradiation apparatus to be used in the present invention.

The ultraviolet irradiation can be carried out preferably by the use of the apparatus shown in FIG. 3. This apparatus can be easily prepared from quartz by reference to FIG. 3.

Figure 2:
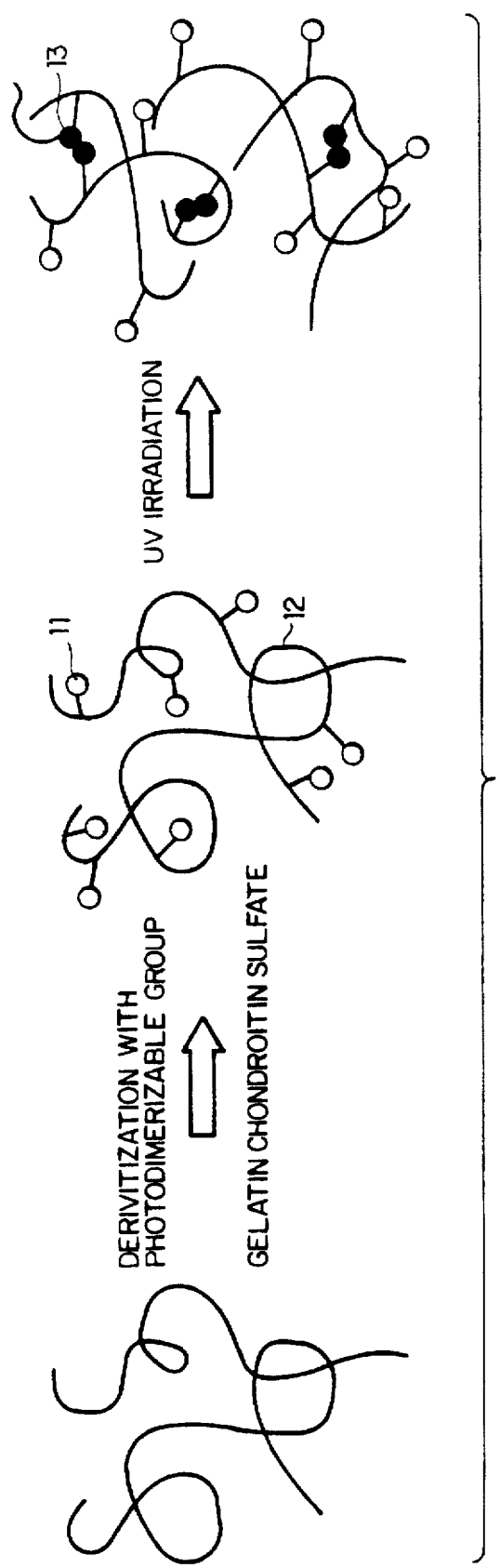
FIG. 2 schematically shows photodimerization steps of coumarin-bound gelatin (C-GT) or cinnamic acid-bound chondroitin sulfate (C-CS) to be used in the present invention.

FIG. 2 conceptually illustrates synthesis of C-CS and C-GT and photocrosslinking (photodimerization) reactions thereof. That is, photodimerizable Cin (A) or Cou (B) group 11 is introduced into CS or GT molecule 10 to effect synthesis of C-CS or C-GT molecule 12 which is then irradiated with ultraviolet light (UV) to form a photodimerized product 13 of Cin (C) or Con (D) groups, thereby effecting synthesis of photogelled C-CS or C-GT 14.

The support to be used in the artificial blood vessel of the present invention is not particularly limited and any material known in the art may be used, provided that it is a porous material which does not prevent organization of the vessel as shown in FIG. 1 and satisfies certain requirements such as no toxicity, no antigenicity, durability and the like. Its illustrative examples include porous materials composed of polyester such as Dacron (trade name) manufactured by Golaski, polyamide such as nylon and the like, polyvinyl such as Ivalon (poly(vinyl formal)) and the like, polyhalogenated olefins such as polytetrafluoroethylene, Teflon (trade name), Gore-Tex (trade name) and the like, polyurethane and silicone rubber. These materials may be used in the form of porous film, woven fabric, non-woven fabric, knitted fabric and the like.

According to the process for producing the artificial blood vessel of the present invention, the vessel may have at least a basic construction in which the photogelled C-CS layer is arranged inside, and the photogelled C-GT layer outside, and C-CS and C-GT may be present as a mixture in the interface area of the C-CS layer and C-GT layer via the support. In order to carry out efficient photocrosslinking reaction, it is preferable to use a two step irradiation process in which first irradiation of light is carried out after arrangement of either the outside C-GT layer or the inside C-CS layer and then second irradiation of light is carried out after arrangement of the remaining layer.

Though not particularly limited, arrangement of each of the aforementioned layers may be effected generally by coating the surface of the support with a solution of C-CS or C-GT dissolved in water or an organic solvent and then fixing the layer to the support by drying to an appropriate level. With regard to the coating method, any usually used method in the art may be used, such as dipping under reduced or normal pressure, centrifugation or the like. Upon coating, a solution of C-CS or C-GT is adjusted to give a concentration ranging from 1 to 20 wt %.

Examples of the present invention are given below by way of illustration and not by way of limitation.

SYNTHESIS EXAMPLE 1

Synthesis of C-CS

A 30 ml portion of dry pyridine was added to 15 ml of DMF in which 247 mg of chondroitin sulfate (molecular weight, 60,000; purified from shark cartilage; manufactured by Seikagaku Corporation) tri-n-butylamine salt had been dissolved, and the mixture was stirred vigorously while adding 59.3 mg of cinnamic acid chloride at room temperature. After 2 hours of reaction at 75° C., ethanol saturated with sodium acetate was added to the reaction solution, and the precipitate thus formed was collected, washed thoroughly with ethanol and then dried under a reduced pressure to obtain 180 mg of C-CS. The C-CS contained 19.0% by weight of cinnamic acid linked thereto, having about 1.0 Cin group per disaccharide repeat unit.

SYNTHESIS EXAMPLE 2

Synthesis of C-GT

A 2.13 g portion of 7-coumaryloxyacetic acid which had been synthesized in accordance with the procedure disclosed in JP-A-3-48674 was dissolved in 20 ml of 1N sodium hydroxide solution. The resulting solution was adjusted to pH 6 with hydrochloric acid and then to a final volume of 30 ml. The 7-coumaryloxyacetic acid solution thus prepared was cooled in an ice bath for 30 minutes and then mixed with two molar quantity (3.71 g) of 1-ethyl-3-(3-dimethylaminopropyl)carbodiimide hydrochloride as a condensing agent. The mixture solution thus prepared was stirred for 1 hour in an ice bath, mixed with 20 ml of phosphate buffer containing 0.5 g of bovine bone gelatin and then stirred overnight (about 24 hours) in an ice bath to synthesize C-GT. Thereafter, the reaction mixture was dialyzed against water for 3 days and lyophilized to recover 0.49 g of C-GT. A total of 27.2 Cou groups were introduced into one molecule of the C-GT.

TEST EXAMPLE 1

Platelet adhesion test of photogelled C-CS or C-GT membrane

The C-CS obtained in Synthesis Example 1 (about 1.0 Cin group per disaccharide repeat unit) or C-GT obtained in Synthesis Example 2 (27.2 Cou groups per one molecule) was made into a membrane on a poly(ethylene terephthalate) (PET) film of 14 mm in diameter and irradiated with ultraviolet light through a filter to cut off wave lengths of equal to and lower than 270 nm (for C-CS) or 310 nm (for C-GT). Films having the thus photogelled C-CS membrane or C-GT membrane were put onto the bottom of wells of a tissue culture dish as well as a control PET film. Platelet rich plasma adjusted to $5 \times 10^8$ platelets per well was added to each of the photogelled membranes and incubated at 37° C. for 1 hour. Each of the resulting films was washed with phosphate buffer and then subjected to fixation with 1.5% glutaraldehyde, conducting staining with 1% osmium, alcohol dehydration, critical point drying and silver-palladium vapor deposition. Thereafter, thus treated films were observed under a scanning electron microscope (S-4000, manufactured by Hitachi, Ltd.) to evaluate the number of adhered platelets and their morphological changes on the film.

A large number of platelets were adhered to the PET film used as a control and the photogelled C-GT membrane, and significant pseudopodium formation and morphological changes were found in the adhered platelets. On the contrary, the number of platelets adhered to the photogelled C-CS membrane was small and their pseudopodium formation and morphological changes were slight.

TEST EXAMPLE 2

Endothelial cell adhesion test of photogelled C-CS or C-GT membrane

The same films having the photogelled C-CS or C-GT membrane prepared in Test Example 1 were put onto the bottom of wells of a tissue culture dish as well as a control PET film. Endothelial cells collected from bovine thoracic aorta were suspended in Dulbecco's modified Eagle's medium (DMEM) supplemented with 15% fetal calf serum, dispensed into the culture dish to a cell density of $4 \times 10^4$ cells per well and then cultured at 37° C. for 4 hours in an atmosphere of 5% $CO_2$. After completion of the culture, the resulting films were treated in the same manner as described in Test Example 1 and then observed under a scanning electron microscope (S-4000, manufactured by Hitachi, Ltd.) to evaluate the number of adhered endothelial cells and their morphological changes on the film.

Similar to the case of platelets, endothelial cells were significantly adhered to and developed on the control PET film and the photogelled C-GT membrane and their adhesion and development were inhibited on the photogelled C-CS membrane.

EXAMPLE 1

Preparation of artificial blood vessel of the invention

An artificial blood vessel made of Dacron (Micro Knit, manufactured by Golaski; porosity, 4,000 ml/cm²/min) having an inside diameter of 5 mm and a length of 5 cm was used as a support, and the C-CS and C-GT used in Test Example 1 were used.

As a first step, the support was fixed to a stainless steel holder and soaked in 10% by weight C-GT aqueous solution under a reduced pressure to effect coating of the compound in interfibrous gaps and on the outer surface of the support. After air-drying, the coated support was irradiated with ultraviolet light ($\lambda > 310$ nm). As a second step, 12.5% by weight C-CS aqueous solution was injected into the resulting support which was subsequently rotated at 600 rpm with its long axis as the center to effect coating of the compound on the inner surface of the support. After air-drying, an optical quartz probe 21 of an ultraviolet light irradiation apparatus 20 shown in FIG. 3 was inserted into thus treated support to carry out irradiation of ultraviolet light ($\lambda > 270$ nm). This ultraviolet light irradiation apparatus 20 is designed in such a manner that ultraviolet light is scattered in radial directions as shown by arrows from the optical quartz probe 21 against optical axis of a mercury-xenon lamp 23 which is cooled by cooling water 22, hence rendering possible irradiation of light inside the support. The artificial blood vessel of the present invention was obtained by repeating this second step several times.

EXAMPLE 2

Implantation and enucleation of artificial blood vessel into and from the living body Under general anesthesia, abdominal aorta under the renal artery of an adult mongrel dog weighing 10 to 13 kg was denuded and the artificial blood vessel of 5 cm in length obtained in Example 1 was transplanted. Anastomosis was effected by continuous suture of 6–0 polypropylene thread. Anticoagulant therapy was not employed except for the use of 100 U/kg of heparin during the operation.

Separately, the same support used in the present invention was pre-clotted with autoblood to form fibrin coat layer and used as a control.

Each artificial blood vessel was enucleated after completion of the predetermined implantation periods (6 hours, 3 days and 7 days). After 4 hours of dipping fixation in 1% glutaraldehyde, each artificial blood vessel was divided at its central position into a sample for use in optical microscope observation and another sample for scanning electron microscope observation use. The sample for use in optical microscopic observation was fixed by dipping it in 10% neutral-buffered formalin aqueous solution, and its sections were subjected to hematoxylin-eosin staining. The sample for use in scanning electron microscopic observation was treated in accordance with the procedure described in the aforementioned test examples.

The artificial blood vessel of the present invention maintained its patency in all cases with no hematoma formation on its peripheral areas. Adhesion of fibrin and blood cell components on the photogelled C-CS membrane inside the vessel were hardly recognizable under the electron microscope after 6 hours, 3 days or 7 days of the implantation, but appearance of the inner surface was changed with the lapse of time due to biodegradation of the photogelled C-CS membrane. When observed under an optical microscope, the photogelled C-CS membrane on the support showed uniformly membrane-like appearance.

After 3 days of the implantation, the photogelled C-GT membrane still remained on the outside of the artificial blood vessel of the present invention and a great number of leukocytes were found on its peripheral areas. However, after 7 days of the implantation, the photogelled C-GT membrane disappeared, leukocytes decreased in number and, in stead, fibroblast-like cells appeared on the periphery of the support fibers and penetrated into interfibrous gaps of the support.

On the other hand, the control artificial blood vessel also maintained its patency in all cases with no hematoma formation on its periphery, but its inner surface was covered by thrombi consisting of numerous platelets, fibrin and leukocytes when observed after 6 hours of the implantation. The inner surface was covered by fibrin net containing erythrocytes and leukocytes after 3 days of the implantation, and the fibrin net was dense and blood cell components were reduced when observed after 7 days of the implantation. On the outer surface of the control artificial blood vessel, thrombi formed due to the pre-clotting treatment still remained after 3 days of the implantation, with leukocytes gathering around the surface. After 7 days of the implantation, the remaining thrombi disappeared, but leukocytes were still present around the outer surface and partly penetrated into intercellular spaces.

Thus, the artificial blood vessel of the present invention, which has been produced based on the different inside and outside designs, showed expected behavior at the acute stage following the concept shown in FIG. 1. Optimization of various characteristics which render possible organization of the artificial blood vessel of the present invention can be attained by specifying physical properties and structures of C-CS and C-GT and photogelled products thereof to be used. In addition, the artificial blood vessel of the present invention is useful as a basic material of other artificial blood vessels such as a hybrid type artificial blood vessel and the like.

While the invention has been described in detail and with reference to specific embodiments thereof, it will be apparent to one skilled in the art that various changes and modifications can be made therein without departing from the spirit and scope thereof.

What is claimed is:

1. An artificial blood vessel which comprises a tubular support having a layer of photogelled cinnamic acid-bound chondroitin sulfate coated on an inner surface thereof and a layer of photogelled coumarin-bound gelatin coated on an outer surface thereof.

2. The artificial blood vessel according to claim 1, wherein said support is made of a porous material selected from the group consisting of polyester, polyamide, polyvinyl, polyhalogenated olefin, polyurethane and silicone rubber.

3. The artificial blood vessel according to claim 1, wherein said chondroitin sulfate is derived from connective tissues of animals and has a molecular weight within a range of from 2,000 to 100,000.

4. The artificial blood vessel according to claim 1, wherein said cinnamic acid-bound chondroitin sulfate contains 0.01 to 3.0 cinnamoyl groups per constitutive disaccharide repeat unit of chondroitin sulfate and said coumarin-bound gelatin contains 5 to 50 coumaryloxymethylcarbonyl groups per molecule.

5. A process for producing an artificial blood vessel, which comprises coating a layer of coumarin-bound gelatin on the outer surface of a tubular support and a layer of cinnamic acid-bound chondroitin sulfate on the inner surface of the support and irradiating each of the layers with light.

6. The process according to claim 5, wherein said light is ultraviolet light.

7. The process according to claim 5, wherein the layer of coumarin-bound gelatin is irradiated with ultraviolet light, from which beams having wave lengths of not more than 310 nm are removed, for 5 to 30 minutes and the layer of cinnamic acid-bound chondroitin sulfate is irradiated with ultraviolet light, from which beams having wave lengths of not more than 270 nm are removed for 5 to 30 minutes.

8. The process according to claim 5, which comprises the steps of:
coating the layer of coumarin-bound gelatin on the outer surface of the tubular support;
irradiating the layer with ultraviolet light to cause photogelation of the layer;
coating the layer of cinnamic acid-bound chondroitin sulfate on the inner surface of the support; and
irradiating the layer with ultraviolet light to cause photogelation of the layer.

* * * * *

UNITED STATES PATENT AND TRADEMARK OFFICE
CERTIFICATE OF CORRECTION

PATENT NO.    : 5,718,723
DATED         : February 17, 1998
INVENTOR(S)   : MATSUDA et al It is certified that error(s) appears in the above-identified patent and that said Letters Patent is hereby corrected as shown below:

On the cover page of the patent in section "OTHER PUBLICATIONS" please add the following references:

-- Matsuda et al, "Photoinduced Prevention of Tissue Adhesion: ASAIO Journal 1992, pp. M154-M157-- and Signed and Sealed this Twenty-fourth Day of August, 1999

*Attest:*

Q. TODD DICKINSON

*Attesting Officer*     Acting Commissioner of Patents and Trademarks